US010716761B2

(12) United States Patent
First et al.

(10) Patent No.: US 10,716,761 B2
(45) Date of Patent: Jul. 21, 2020

(54) INGESTIBLE MEDICAL DELIVERY DEVICES

(71) Applicant: Alcresta Therapeutics, Inc., Newton, MA (US)

(72) Inventors: Eric First, Morristown, NJ (US); David Widom, Long Valley, NJ (US)

(73) Assignee: Alcresta Therapeutics, Inc., Newton, MA (US)

( * ) Notice: Subject to any disclaimer, the term of this patent is extended or adjusted under 35 U.S.C. 154(b) by 0 days.

(21) Appl. No.: 16/042,683

(22) Filed: Jul. 23, 2018

(65) Prior Publication Data
US 2019/0022015 A1 Jan. 24, 2019

Related U.S. Application Data

(60) Provisional application No. 62/536,200, filed on Jul. 24, 2017.

(51) Int. Cl.
| | |
|---|---|
| *A61K 9/48* | (2006.01) |
| *A61K 9/50* | (2006.01) |
| *A61K 9/24* | (2006.01) |
| *A61M 31/00* | (2006.01) |
| *A61K 45/06* | (2006.01) |
| *A61J 3/07* | (2006.01) |
| *A61J 7/00* | (2006.01) |
| *A61K 31/12* | (2006.01) |
| *A61J 1/20* | (2006.01) |
| *A61K 31/05* | (2006.01) |
| *A61K 31/122* | (2006.01) |
| *A61K 36/9066* | (2006.01) |
| *A61K 31/202* | (2006.01) |
| *A23L 33/115* | (2016.01) |
| *A61K 31/4045* | (2006.01) |
| *A23L 33/12* | (2016.01) |
| *A61K 31/198* | (2006.01) |
| *A61K 33/06* | (2006.01) |

(52) U.S. Cl.
CPC .......... *A61K 9/4808* (2013.01); *A23L 33/115* (2016.08); *A23L 33/12* (2016.08); *A61J 1/2093* (2013.01); *A61J 3/07* (2013.01); *A61J 7/0053* (2013.01); *A61K 9/209* (2013.01); *A61K 9/48* (2013.01); *A61K 9/4833* (2013.01); *A61K 9/5073* (2013.01); *A61K 9/5084* (2013.01); *A61K 31/05* (2013.01); *A61K 31/12* (2013.01); *A61K 31/122* (2013.01); *A61K 31/198* (2013.01); *A61K 31/202* (2013.01); *A61K 31/4045* (2013.01); *A61K 33/06* (2013.01); *A61K 36/9066* (2013.01); *A61K 45/06* (2013.01); *A61M 31/00* (2013.01); *A61M 31/002* (2013.01); *A61J 3/072* (2013.01)

(58) Field of Classification Search
CPC . A23L 33/115; A23L 33/12; A61J 3/07; A61J 1/2093; A61K 9/209; A61K 9/48; A61M 31/002

See application file for complete search history.

(56) References Cited

U.S. PATENT DOCUMENTS

| | | | |
|---|---|---|---|
| 2,798,024 A | 7/1957 | Zapapas et al. | |
| 4,142,526 A | 3/1979 | Zaffaroni et al. | |
| 4,522,625 A | 6/1985 | Edgren | |
| 5,443,459 A | 8/1995 | Wong et al. | |
| 5,976,571 A | 11/1999 | Crison et al. | |
| 6,245,357 B1 | 6/2001 | Edgren et al. | |
| 6,303,144 B1 | 10/2001 | Omura | |
| 6,630,165 B2 | 10/2003 | Seroff et al. | |
| 7,670,612 B2 | 3/2010 | Miller | |
| 8,361,497 B2 | 1/2013 | Miller | |
| 8,361,498 B2 | 1/2013 | McAllister et al. | |
| 8,440,224 B2 | 5/2013 | Clarke et al. | |
| 8,591,947 B2 | 11/2013 | Vergez et al. | |
| 9,241,911 B2 | 1/2016 | Miller | |
| 9,456,987 B2 | 10/2016 | Van Rooyen et al. | |
| 9,539,216 B2 | 1/2017 | Miller | |
| 2004/0109894 A1* | 6/2004 | Shefer .................. | A61K 9/1635 424/469 |
| 2005/0260264 A1 | 11/2005 | Edgren et al. | |
| 2007/0087048 A1 | 4/2007 | Abrams et al. | |
| 2009/0118579 A1 | 5/2009 | Duerschinger | |
| 2009/0148514 A1 | 6/2009 | Matthews et al. | |
| 2010/0183713 A1 | 7/2010 | Tsutsumi et al. | |
| 2011/0129504 A1* | 6/2011 | Neves Garcia Da Silva Reis ...... | A61K 9/0053 424/400 |

(Continued)

FOREIGN PATENT DOCUMENTS

| | | |
|---|---|---|
| JP | 05025037 A | 2/1993 |
| JP | 07173052 A | 7/1995 |

(Continued)

*Primary Examiner* — Mark V Stevens

(74) *Attorney, Agent, or Firm* — Bookoff McAndrews, PLLC

(57) ABSTRACT

Exemplary embodiments of the disclosure may be drawn to ingestible delivery devices. An ingestible delivery device may include a first compartment and a second compartment. A lipase may be contained within the first compartment, and a fat may be contained within the second compartment. The first compartment may be sealed from the second compartment prior to exposure to a trigger, preventing the lipase and the fat from contacting each other, and at least one of the first compartment or the second compartment may at least partially rupture upon exposure to the trigger, allowing the lipase and the fat to contact each other.

20 Claims, 4 Drawing Sheets

(56) References Cited

U.S. PATENT DOCUMENTS

2014/0364352 A1    12/2014    Walls et al.

FOREIGN PATENT DOCUMENTS

| WO | WO 2013/123139 A1 | 8/2013 | |
|---|---|---|---|
| WO | WO-2013123139 A1 * | 8/2013 | |
| WO | WO 2017/062954 A1 | 4/2017 | |
| WO | WO-2017062954 A1 * | 4/2017 | ........... A61K 9/4808 |

* cited by examiner

INGESTIBLE MEDICAL DELIVERY DEVICES

CROSS-REFERENCE TO RELATED APPLICATIONS

This application claims the benefits of priority from U.S. Provisional Application No. 62/536,200, filed on Jul. 24, 2017, the entirety of which is incorporated herein by reference.

BACKGROUND

Fatty acids, e.g., long-chain fatty acids, are important to human health and development. Many fatty acids are consumed as triglycerides, in which three long-chain fatty acids are bound to a glycerol molecule via ester linkages. Absorption of triglycerides by the body first requires the enzymatic action of lipases (e.g., pancreatic lipase) and bile salts, which digest triglycerides through hydrolysis, breaking them down into a monoglyceride and two free fatty acids. Digestion products consisting of a mixture of tri-, di-, and monoglycerides and free fatty acids, which, together with the other fat soluble contents of the diet (e.g., the fat soluble vitamins and cholesterol) and bile salts, form mixed micelles in the watery duodenal contents. Once broken down, the monoglycerides and free fatty acids may be absorbed by enterocytes—epithelial cells lining the small intestine—for example, in the region of the jejunum. The contents of these micelles (but not the bile salts) enter the enterocytes where they are resynthesized into triglycerides and packaged into chylomicrons, which are released into the lacteals (the capillaries of the lymph system of the intestines). Medium-chain triglycerides are absorbed directly into the bloodstream.

Patients suffering from various malabsorption impairments may be unable to adequately digest triglycerides and other forms of fat through hydrolysis, inhibiting absorption of the fatty acids required to maintain health. Further, patients may have one or more impairments that may be ameliorated by the uptake of free fatty acids, triglycerides, and/or other forms of fat. Exemplary impairments include, but are not limited to, the following: traumatic brain injury (TBI), concussion, Alzheimer's, compromised pancreatic output, acute and chronic pancreatitis, pancreatic cancer, pancreatic insufficiency, cystic fibrosis, cerebral palsy, irritable bowel syndrome, chronically abnormal epithelium, amyloidosis, celiac disease, Crohn's disease, ischemia, radiation enteritis, tropical sprue, Whipple disease, inadequate gastric mixing, rapid emptying, or both, Billroth II gastrectomy, gastrocolic fistula, gastroenterostomy, insufficient digestive agents, biliary obstruction and cholestasis, cirrhosis, chronic pancreatitis, cholestyramine-induced bile acid loss, cystic fibrosis, lactase deficiency, pancreatic cancer, pancreatic resection, sucrase-isomaltase deficiency, abnormal milieu, abnormal motility secondary to diabetes, scleroderma, hypothyroidism, or hyperthyroidism, bacterial overgrowth due to blind loops (deconjugation of bile salts), diverticula in the small intestine, Zollinger-Ellison syndrome (low duodenal pH), acutely abnormal epithelium, acute intestinal infections, alcohol, neomycin, impaired transport, abetalipoproteinemia, Addison disease, blocked lacteals due to lymphoma or tuberculosis, intrinsic factor deficiency (as in pernicious anemia), lymphangiectasia, jejunoileal bypass for obesity, or other conditions. Other patients may need or want additional dietary supplementation. Pancreatic enzyme replacement therapy ("PERT") pills containing lipase enzymes may be consumed to improve the hydrolysis of triglycerides. Typically, PERTs are taken prior to eating and/or after eating.

However, these PERTs appear to not work or work inefficiently. Hence a need exists to overcome the deficiencies of PERTs and/or address the needs of patients unable to adequately digest triglycerides and other forms of fat.

SUMMARY

Exemplary embodiments of the disclosure may be drawn to ingestible delivery devices. An ingestible delivery device may include a first compartment and a second compartment. A lipase may be contained within the first compartment, and a fat may be contained within the second compartment. The first compartment may be sealed from the second compartment prior to exposure to a trigger, preventing the lipase and the fat from contacting each other, and at least one of the first compartment or the second compartment may at least partially rupture upon exposure to the trigger, allowing the lipase and the fat to contact each other.

Various embodiments of the delivery device may include one or more of the following features. The delivery device may include an exterior layer surrounding the first compartment and the second compartment; and a barrier wall may form a boundary between the first compartment and the second compartment. The delivery device may include a third compartment and at least one of a protein, a protease, a carbohydrate, or an amylase contained within the third compartment. The delivery device may include a fourth compartment and at least one of a protein, a protease, a carbohydrate, or an amylase contained within the fourth compartment. The first compartment may be contained within the second compartment; at least one of the first compartment and the second compartment may contain a second barrier wall; the fat may include a structured lipid; the fat may include a long-chain fatty acid; and the trigger may be at least one of a neutral pH or an alkaline pH.

In other exemplary embodiments, an ingestible delivery device may include a plurality of compartments. A lipase may be contained within a first compartment of the plurality of compartments, and a fat may be contained within a second compartment of the plurality of compartments. A barrier wall may separate the first compartment from the second compartment, wherein the barrier wall separates the lipase and the fat when the barrier wall is in a first state, and wherein the barrier wall at least partially degrades to expose the lipase to the fat when the barrier wall is in a second state.

Various embodiments of the delivery device may include one or more of the following features. The barrier wall may transition from the first state to the second state upon exposure to a trigger; the trigger may be a compressive pressure applied to the device; the trigger may be a compressive pressure applied to the device, prior to ingestion; the trigger may be at least one of a neutral pH or an alkaline pH; the trigger may be at least one of a neutral pH or an alkaline pH, applied after ingestion; the fat may include a structured lipid; the fat may include a long-chain fatty acid; the fat may include a medium-chain fatty acid; the fat may include a short-chain fatty acid; the fat may include at least two of a long-chain fatty acid, a medium-chain fatty acid, or a short-chain fatty acid; the delivery device may further include a third compartment of the plurality of compartments, wherein the third compartment contains at least one of a protease or an amylase; and the delivery device may further include a fourth compartment, wherein the fourth compartment contains at least one of a protein or a carbohydrate.

In other exemplary embodiments, an ingestible delivery device may include a first compartment containing a fat, a second compartment containing a lipase, a third compartment containing a protein, and a fourth compartment containing a protease. The fat in the first compartment, the lipase in the second compartment, the protein in the third compartment, and the protease in the fourth compartment may remain separate from one another when the device is in a first state, and at least one of the first compartment, the second compartment, the third compartment, or the fourth compartment may at least partially degrade when the device is in a second state.

Various embodiments of the delivery device may include one or more of the following features. The device may transition to the second state when exposed to at least one of a neutral pH or an alkaline pH; the device may further include an exterior coating; and the second compartment may be contained within the first compartment, and the fourth compartment may be contained within the third compartment.

Still other exemplary embodiments may be drawn to methods. An exemplary method may include administering an ingestible delivery device to a subject suspected of traumatic brain injury. The ingestible delivery device may comprise a first compartment, a second compartment, a lipase contained within the first compartment, and a fat contained within the second compartment. The first compartment may be sealed from the second compartment prior to exposure to a trigger, preventing the lipase and the fat from intermixing. At least one of the first compartment or the second compartment may at least partially rupture upon exposure to the trigger, allowing the lipase and the fat to intermix with each other so that the lipase hydrolyzes the fat, forming free fatty acids and monoglycerides. The trigger may cause the ingestible delivery device to rupture in the digestive tract of the subject, delivering free fatty acids and monoglycerides to the digestive tract of the subject.

Various embodiments of the method may include one or more of the following features. The ingestible delivery device may be administered to the subject at least 4 hours after the subject last ate food and/or without food; the ingestible delivery device may be administered to the subject with water; the ingestible delivery device may be administered to the subject within 1 hour of an event that caused the suspected traumatic brain injury; the trigger may cause the ingestible delivery device to rupture in a small intestine of the subject, delivering free fatty acids and monoglycerides to the small intestine of the subject; or the fat may be an omega-3 fatty acid, and the device may further comprise at least one of resveratrol, curcumin, magnesium, co-enzyme Q10, turmeric, or creatine.

Another exemplary method may include administering an ingestible delivery device to a subject who has not eaten food for at least 4 hours. The ingestible delivery device may comprise a first compartment, a second compartment, a lipase contained within the first compartment, and a fat contained within the second compartment. The first compartment may be sealed from the second compartment prior to exposure to a trigger, preventing the lipase and the fat from intermixing. At least one of the first compartment or the second compartment may at least partially rupture upon exposure to the trigger, allowing the lipase and the fat to intermix with each other so that the lipase hydrolyzes the fat, forming free fatty acids and monoglycerides. The trigger may cause the ingestible delivery device to rupture in the digestive tract of the subject, delivering free fatty acids and monoglycerides to the digestive tract of the subject.

Various embodiments of the method may include one or more of the following features. The ingestible delivery device may be administered to the subject with water and/or without food; the ingestible delivery device may be administered to the subject within 1 hour of an event that caused suspected traumatic brain injury; the trigger may cause the ingestible delivery device to rupture in a small intestine of the subject, delivering free fatty acids and monoglycerides to the small intestine of the subject; or the fat may be an omega-3 fatty acid, and the device may further comprise at least one of resveratrol, curcumin, magnesium, co-enzyme Q10, turmeric, or creatine Both the foregoing general description and the following detailed description are exemplary and explanatory only and are not restrictive of the features, as claimed. As used herein, the terms "comprises," "comprising," "includes," or other variations thereof, are intended to cover a non-exclusive inclusion such that a process, method, article, or apparatus that comprises a list of elements does not include only those elements, but may include other elements not expressly listed or inherent to such a process, method, method of treatment, article, or apparatus. Additionally, the term "exemplary" is used herein in the sense of "example," rather than "ideal." It should be noted that all numeric values disclosed or claimed herein (including all disclosed values, limits, and ranges) may have a variation of +/−10% (unless a different variation is specified) from the disclosed numeric value. Moreover, in the claims, values, limits, and/or ranges means the value, limit, and/or range +/−10%.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. There are many aspects and embodiments described herein. Those of ordinary skill in the art will readily recognize that the features of a particular aspect or embodiment may be used in conjunction with the features of any or all of the other aspects or embodiments described in this disclosure. In the drawings.

DETAILED DESCRIPTION

Figure 1:
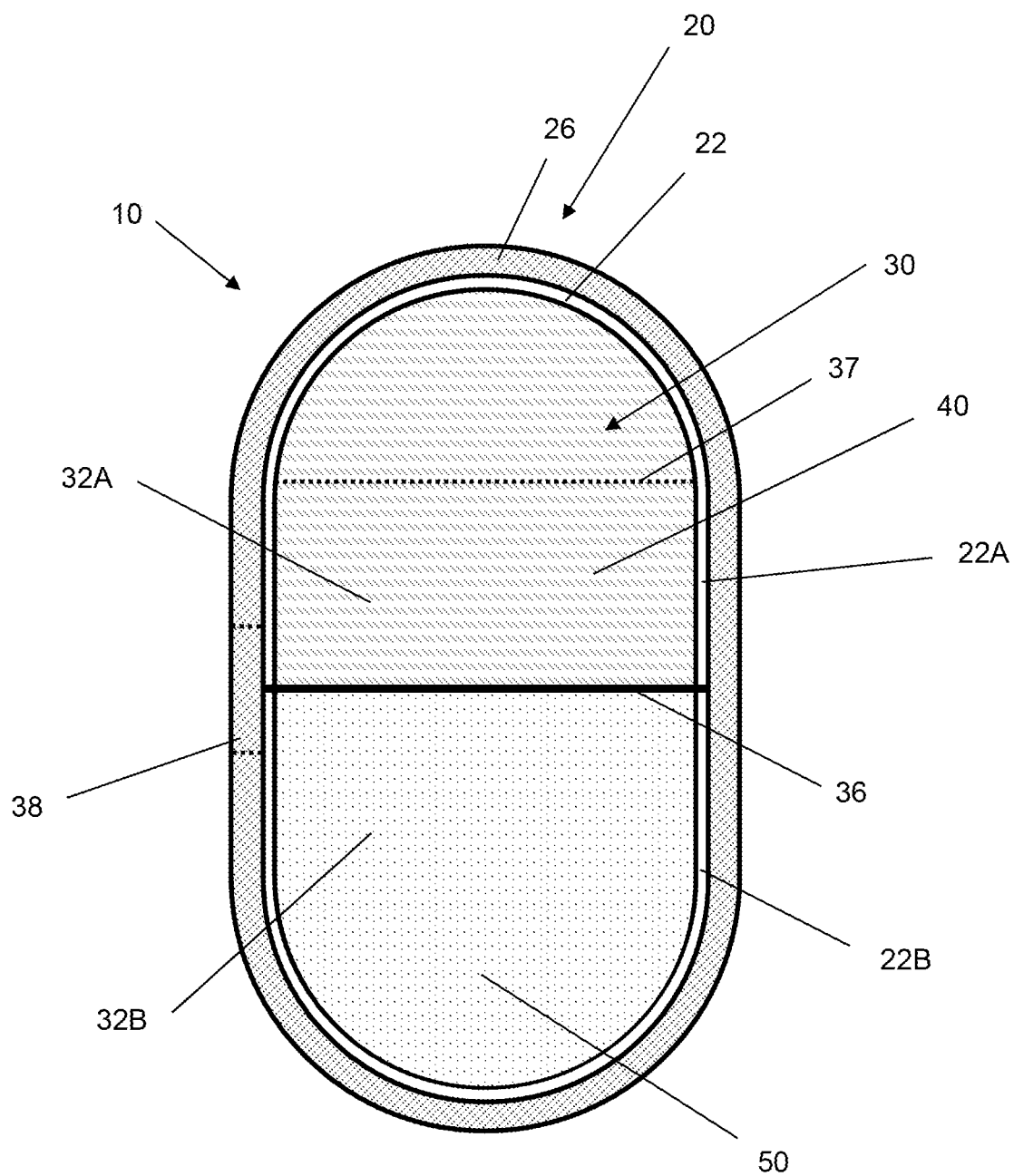
FIG. 1 depicts an exemplary delivery device, according to various embodiments of the present disclosure.

Reference will now be made in detail to the exemplary embodiments of the present disclosure described below and illustrated in the accompanying drawings. Wherever possible, the same reference numbers will be used throughout the drawings to refer to same or like parts.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

With PERT pills, the lipase enzymes can only interact with fats ingested by a consumer if the PERT pills and the fats are located in the same region of the body at the same time. But, even if the PERT pills are administered when eating, the food may be digested at a different rate than the PERT pills. This may potentially cause a mismatch within the body between the location of the PERT pills and concomitant enzymes and the location of the fats that need to be broken down. For example, absorption of fats mainly occurs in the mid-section of the jejunum, and thus the lipase component of PERT would have to be bioavailable at the same time and place as where the fats from the food are broken down. Accordingly, the lipase and the fats would need to reach the same region of the jejunum at the same time. By contrast, proteins are broken down and absorbed earlier and in more proximal parts of the GI tract. As an example of this mismatch, in a typical person, fats take up to six hours for complete digestion and storage in fat cells compared to proteins, which can be absorbed in as little as one hour.

Because of the discrepancy, the enzymes delivered in the PERT pills may not be able to act on the ingested fats, or may have decreased efficiency. Consuming additional amounts of lipase enzymes may reduce the likelihood of such mismatches, but larger dosages of lipase enzymes may cause negative side effects for the consumer, including, but not limited to, abdominal distension, gas, steatorrhea, abdominal pain, and other gastrointestinal symptoms. PERT dosing is also limited due to potential of fibrosing colonopathy, as indicated in PERT product inserts.

As a result, even individuals who take PERT pills regularly may be unable to hydrolyze and absorb the desired amount of fats. Further improvements are required to address these and other known issues.

Aspects of the present disclosure are described with reference to delivery devices for releasing substances, e.g., medicaments and/or nutritional supplements. Embodiments of the disclosure are drawn to consumable pills including one or more compartments. Exemplary compartment and content configurations are described below with reference to various enzymes, lipids, fats, triglycerides, fatty acids, including long-chain fatty acids, medium-chain fatty acids, short-chain fatty acids, proteins, amylases, proteases, and other materials. References to a particular number of compartments (e.g., one or two compartments), a particular content or combination of contents (e.g., a fatty acid and/or a lipase enzyme), a particular result from mixing the contents (e.g., hydrolysis), or a particular location of the mixing of contents (e.g., within the intestines), are provided for convenience and are not intended to limit the present disclosure unless claimed. For example, delivery devices of the present disclosure may include any suitable number and/or configuration of compartments, and any suitable number or combination of contents (stored in any suitable way within the compartments). Further, depending on the type of contents stored within the compartments, any suitable reaction type may occur when the contents are released from the compartment(s) and exposed to one another. Additionally, exemplary delivery devices may be configured to degrade immediately after consumption, after a delayed period of time, in response to certain trigger environments, or over a prolonged period of time, allowing the devices to be designed to break down in any suitable region of the body.

Aspects of the present disclosure are, at times, described as being taken without food and/or on an empty stomach. Generally speaking, the human stomach is empty approximately 4-5 hours after having eating a meal, thus the human stomach may be empty approximately 4 hours after having eaten food. It will be understood that aspects of the present disclosure may provide benefits to patients by being able to be taken without food, on an empty stomach (e.g., 4 or more hours after having eaten), and/or with water or other liquids.

Aspects of this disclosure are now described with reference to a delivery device 10, depicted in FIG. 1 as a pill dimensioned for oral consumption. Device 10 (and the other devices disclosed herein) may be configured to treat patients with lipase deficiencies and/or malabsorption or patients having other impairments. Device 10 may be used instead of, or in addition to, other treatments, such as PERT pills including lipase enzymes. Device 10 may be used as a point-of-care device, may be sold as a prescription, and/or may be sold over-the-counter. In some aspects, device 10 may be ingested by a patient without food and/or on an empty stomach, whereas in other embodiments, device 10 may be ingested with food.

As described herein, device 10 may include multiple compartments for separately storing at least one fat and at least one lipase and may have a structure that allows the contents of the compartments to mix at a given time and/or place or in response to a given event. For example, a fat may be stored in one compartment, and a lipase may be stored in another, separate compartment prior to ingestion and/or immediately following ingestion. Once within the body, however, one or more of the compartments may degrade, allowing the fat and the lipase to mix with one another. In some aspects, device 10 may be configured to allow the contents of its compartments to mix once device 10 reaches a certain location within the body, e.g., the small intestine or large intestine (collectively intestine) of the consumer. Mixture of a fat and a lipase stored in device 10 may cause the lipase to hydrolyze the fat. Accordingly, device 10 may promote the delivery to and uptake of hydrolyzed fats (e.g., free fatty acids and monoglyceride) in the body or in a targeted region of the body, e.g., the intestine. Similar results may be obtained with other enzymes and supplements stored within the compartments of device 10, as is described further below.

As shown in FIG. 1, device 10 may include an exterior layer 20 and an interior core 30. Exterior layer 20 may include one or more coatings or layers surrounding interior core 30. In FIG. 1, the one or more coatings or layers includes a capsule shell 22 formed by joining two portions 22A and 22B, and an exterior coating 26 surrounding capsule shell 22. Portions 22A and 22B may be joined together using, e.g., one or more of an adhesive, an exterior band, material fusion, mechanical connections, a heat seal, a friction fit (e.g., corresponding rims that friction-fit together or corresponding grooves and projections), chemical bonds, or any suitable connection mechanism. In FIG. 1, portions 22A and 22B are joined to one another by exterior coating 26.

It is understood that although portions 22A and 22B are depicted as forming capsule shell 22, and that these layers are distinguished from coating 26, exterior layer 20 may consist of a single shell or may comprise additional layers or different configurations of layers.

Capsule shell 22 and coating 26 may form a continuous barrier surrounding interior core 30 from an external environment. In some embodiments, the barrier may be insoluble to water, saliva, alkaline environments, acidic environments, and/or other materials and may withstand initial ingestion by a consumer. For example, in some embodiments, the barrier may be insoluble in an acidic environment to allow device 10 to pass through the stomach without being compromised by gastric acids. In some embodiments, at least portions of the barrier may be soluble in a neutral to alkaline environment to, for example, degrade the barrier and expose the contents of interior core 30 when device 10 is in the small intestine.

In some embodiments, bicarbonate or other alkaline agents may be incorporated into the physical compartment or as an excipient within one of more of the compartments to control release of the compartment contents only when device 10 reaches the appropriate absorption region of the intestine. In some embodiments, acidic agents may be incorporated into the physical compartment or as an excipient within one of more of the compartments to control release of the compartment contents until only when device 10 reaches the appropriate absorption region of the intestine, depending on the target release area.

Portions 22A and 22B and/or coating 26 may be made of the same material or of different materials or combinations of materials. Exemplary materials may include, e.g., a polymeric material, such as an enteric polymer. In some embodiments, one or more openings may be formed in coating 26 and/or in portions 22A and 22B upon exposure to a trigger (e.g., an environment that causes one or more portions of coating 26 and/or portions 22A and 22B to dissolve). The openings may be configured to dissolve upon exposure to a trigger to release the contents of interior core 30. In some embodiments, the openings may be designed as weaknesses in the barrier, e.g., a thinning of the barrier, a portion of material that is different from the surrounding barrier material, a seam or weakness defining a break-away portion, or other suitable structure. Exemplary triggers may include, e.g., exposure to a neutral environment, an alkaline environment, an acidic environment, a type of chemical or enzyme, the passage of a given amount of time, and/or pressure applied to device 10. In some embodiments, however, no openings may be included, and the entire barrier and/or portions of the barrier not previously defined may break down in response to a trigger.

In some embodiments, coating 26 may include a first material having a first dissolution rate in response to a trigger (e.g., a neutral to alkaline environment), and portions 22A and 22B may include a second material having a second dissolution rate in response to the trigger. The first and second dissolution rates may be different, e.g., coating 26 may dissolve more quickly in response to a trigger than portions 22A and 22B, or vice versa. In some embodiments, portions 22A and 22B may have different dissolution rates from each other. It is also contemplated that coating 26, and one or both of portions 22A and 22B may dissolve in response to different triggers.

Interior core 30 may include one or more compartments. Interior core 30 of FIG. 1, for example, includes a first compartment 32A defined by interior surfaces of portion 22A of exterior layer 20, and a second compartment 32B defined by interior surfaces of portion 22B of exterior layer 20. First compartment 32A may contain an enzyme 40, e.g., a lipase, and second compartment 32B may contain fat 50, e.g., a fatty acid (for example, a long-chain fatty acid in the form of a triglyceride). First compartment 32A and second compartment 32B may be separated from one another by a barrier wall 36 extending between the two compartments, keeping enzyme 40 in first compartment 32A separate from fat 50 in second compartment 32B.

Although first and second compartments 32A and 32B are depicted as being approximately equal in size in FIG. 1, it is understood that the compartments may be different sizes and that barrier wall 36 may separate the compartments along any portion of device 10 and at any orientation. Barrier wall 36 may have any suitable shape or location. For example, barrier wall 36 may be a planar element that bisects interior core 30, as in FIG. 1, or it may be a curved element positioned closer to one end of interior core 30, as in FIGS. 2A-2C. Barrier wall 36 may extend along a width or a length of interior core 30, or may extend along an angle. Barrier wall 36 may be undulated, rounded, planar, may be irregular in shape, or may be any other suitable shape. Portions of barrier wall 36 or all of barrier wall 36 may be soluble in response to a trigger (e.g., a neutral and/or alkaline environment). In some embodiments, barrier wall 36 may have a dissolution rate that is the same as that of exterior layer 20 or a dissolution rate that is different than exterior layer 20.

Figure 2A:
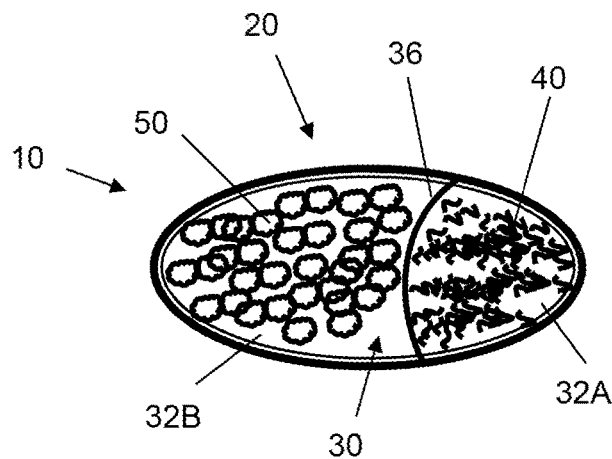
FIGS. 2A-2C depict an exemplary opening sequence of an exemplary delivery device, according to various embodiments of the present disclosure.
Figure 2B:
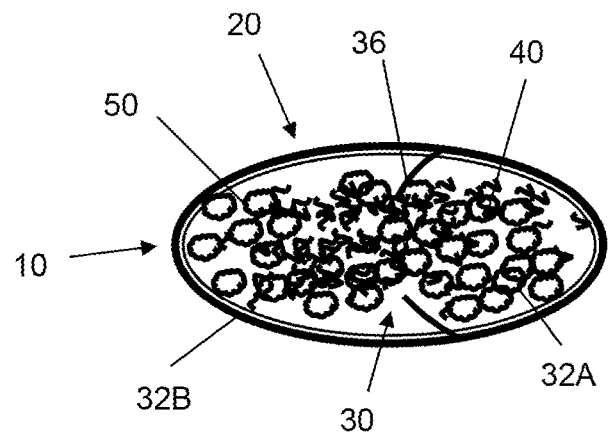

In the embodiment of FIG. 1, first and second compartments 32A and 32B may be approximately equal in size and may contain approximately equal amounts of enzyme 40 and fat 50. In various embodiments, however, first compartment 32A may be smaller or larger to accommodate more or less of enzyme 40, e.g., depending upon the efficacy of enzyme 40. For example, in FIGS. 2A and 2B, a smaller amount of enzyme 40 may be contained and then released in order to hydrolyze a larger amount of fat 50. In some embodiments, however, the size of the relative compartments may not correlate to the amount of enzyme 40 or fat 50 contained within the respective compartment. Additionally, although FIGS. 2A and 2B depict enzyme 40 contained within the smaller compartment, the locations of fat 50 and enzyme 40 may be switched, and fat 50 may be contained within the smaller compartment.

In some embodiments, the amount of enzyme 40 may be enough to hydrolyze fat 50 contained within device 10, as well as additional enzyme to hydrolyze fats that may be present in the intestines (e.g., small intestines) of the consumer, e.g., fats found in food ingested previously, food ingested with device 10, and/or food ingested following ingestion of device 10. In some embodiments, device 10 may be taken without food and/or on an empty stomach. For example, device 10 may be taken on an empty stomach (e.g., taken on an empty stomach with water and/or fluids to facilitate swallowing of device 10). The ability to ingest device 10 on an empty stomach and/or without food may, in some applications, overcome issues associated with reduced uptake of lipids when taken without food, as will be described in further detail below.

As described above, first compartment 32A may contain enzyme 40, and second compartment 32B may contain fat 50. Enzyme 40 may include one or more lipase enzyme, and fat 50 may include one or more structured lipids, fatty acids, etc. In some embodiments, the lipase may include one or more of, e.g., a *Chromobacterium viscosum, Pseudomonas fluorescens, Burcholderia cepacia*, or *Rhizopus oryzae* lipase, or any other suitable wild-type or recombinant lipase or combination thereof. Fat 50 may include one or more of, e.g., a short-chain fatty acid, a medium-chain fatty acid, and/or long-chain fatty acid, for example, a long-chain polyunsaturated fatty acid ("LC-PUFA") triglyceride, or a combination thereof. Exemplary fats may include natural or structured lipids, or omega-3 fatty acids, like docosahexaenoic acid ("DHA"), eicosapentaenoic acid ("EPA"), alpha-linolenic acid ("ALA"), arachidonic acid ("ARA" or "AA"), and/or linoleic acid ("LA"). Any suitable combination of fat and enzyme may be included in device 10. In some embodiments, fat 50 may be in the form of fish oil. In other embodiments, fat 50 may be from a plant source alone or in combination with fish oil.

In an exemplary embodiment, the quantity of lipase enzyme included in device 10 may be predicated on the quantity of fats in device 10 and/or the quantity of fats in device 10 as well as additional lipase for hydrolysis of at least some of the fats consumed by the person ingesting device 10.

In an exemplary embodiment, a lipase enzyme and a fat, e.g., a structured lipid, may be separately contained in first compartment 32A and second compartment 32B, respectively. The lipase and the fat may be kept separate from one another and may not be able to come into contact with each other and/or react with one another when contained in their respective compartments. However, upon dissolution of barrier wall 36 or one or more portions of barrier wall 36, the contents of first and second compartments 32A and 32B may be allowed to mix and/or to come into contact with one another. The breakdown of barrier wall 36 may therefore allow the lipase to react with the fat and to hydrolyze the fat.

In some embodiments, enzyme 40 and fat 50 may be stored within their respective compartments in the same form or may be stored in different forms relative to one another. For example, first compartment 32A may include a gel, liquid, solid, powder, or combination thereof, including enzyme 40. Second compartment 32B may include a second gel, liquid, solid, or combination thereof, including fat 50. First and second compartments 32A and 32B may both include a gel, liquid, solid, powder, or combination thereof, or they may both include different forms of matter. In some embodiments, the form of either or both of enzyme 40 and fat 50 may prevent them from interacting with each other. For example, one or both may be stored in a solid phase or a gel phase that inhibits and/or slows interaction between the two until device 10 breaks down.

It is contemplated that other contents may also be included with enzyme 40 and fat 50 in device 10. For example, enzyme 40 and/or fat 50 may be contained with at least one of a protein, a protease enzyme, an amylase enzyme, a simple liquid, or a carbohydrate. In some embodiments, these separate substances may be stored in the same compartments as enzyme 40 and fat 50, or may have their own separate compartments. In some embodiments, the other component(s) may be stored in an enclosed container (e.g., capsule) within the same compartment that stores enzyme 40, fat 50, or another components, so that although multiple, smaller components are nested within same compartment, the contents are kept separate from one another.

Figure 2C:
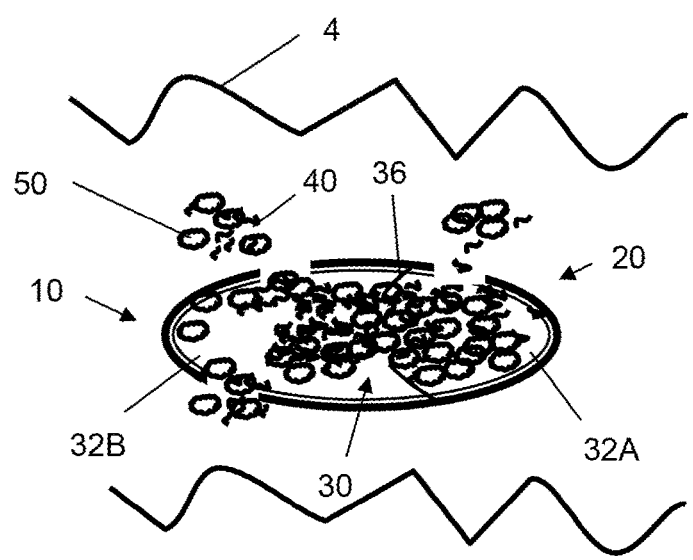

Exemplary opening sequences for compartments 32A and 32B are depicted in reference to the embodiments of FIGS. 2A-2C. In FIG. 2A, barrier wall 36 is in tact, keeping the first and second compartments 32A and 32B closed, and keeping enzyme 40 separate from fat 50. Because of exterior layer 20, the first and second compartments 32A and 32B may remain closed to the outside environment (e.g., an acidic environment). Such an embodiment may be used to, for example, prevent mixing of enzyme 40 and fat 50 in the acidic environment of the stomach, where a portion of enzyme 40 or all of enzyme 40 may be neutralized, denatured, and/or inactivated by gastric acids. In some embodiments, a polymeric material like an enteric coating may be included in exterior layer 20 to maintain the integrity of exterior layer 20 in the stomach.

Barrier wall 36 may be opened before, after, or at the same time as compartments 32A and 32B, allowing enzyme 40 to mix with fat 50 inside of interior core 30. In FIG. 2B, barrier wall 36 is shown opening before portions of exterior layer 20 dissolve, allowing enzyme 40 to mix with fat 50 inside of interior core 30. In other embodiments, however, exterior layer 20 may dissolve before barrier wall 36 and/or compartments 32A and 32B or at the same time, allowing enzyme 40 to mix with fat 50 in the surrounding environment.

Barrier wall 36 may open in response to any suitable trigger. For example, device 10 may be compressible, and barrier wall 36 may opened when a sufficient amount of compressive force is applied to exterior layer 20, rupturing barrier wall 36. Such forces may, for example, be applied by squeezing device 10 between two fingers before consumption, and/or by natural contractions of the stomach and/or intestines, e.g., peristalsis. The application of a compressive force above a certain threshold may cause barrier wall 36 to rupture, allowing enzyme 40 to interact with fat 50. In the embodiment in which device 10 is squeezed by the consumer before being swallowed, enzyme 40 and fat 50 may interact prior to ingestion. Additionally or alternatively, barrier wall 36 may dissolve inside of interior core 30 after a predetermined period of time. For example, a portion of barrier wall 36 may become soluble with one or both of enzyme 40 or fat 50 when exposed to natural body temperatures for a predetermined period of time, or may dissolve when exposed to natural body temperatures for a predetermined period of time. In some instances, barrier wall 36 may open, enabling fat 50 and enzyme 40 to mix. Mixing may be encouraged by digestive movement, for example, taking advantage of the natural turbulent environment caused by digestion.

However barrier wall 36 is opened, enzyme 40 may hydrolyze fat 50 within interior core 30 once enzyme 40 and fat 50 are mixed. As shown in FIG. 2C, the hydrolyzed fats may be released into the body when portions of exterior layer 20 dissolve or when the entirety of exterior layer 20 dissolves, opening the first and/or second compartments 32A and 32B at various locations (if first and second compartments 32A and 32B are still in tact). In some embodiments, first and/or second compartments 32A and 32B may be opened once device 10 reaches the intestines, e.g., the small intestine.

In some embodiments, first and second compartments 32A and 32B may be opened when portions of exterior layer 20 dissolve in response to a trigger (e.g., in response to an alkaline or neutral environment), allowing enzyme 40 to mix with fat 50 inside and/or outside of interior core 30. For example, exterior layer 20 and barrier wall 36 may be soluble in response to a trigger at comparable dissolution rates, so that compartments 32A and 32B are opened at approximately the same time. Different dissolution rates may be used to modify the opening sequence of device 10. For example, a portion of exterior layer 20 adjacent the connection between portions 22A and 22B of capsule shell 22 may have a dissolution rate that is faster than the remainder of exterior layer 20, allowing portions 22A and 22B to be split open, rupturing barrier wall 36, and causing all or most of enzyme 40 and fat 50 to spill out of compartments 32A and 32B. Hydrolysis may then occur inside or outside of interior core 30, as enzyme 40 and fat 50 are mixed in the trigger environment.

Figure 3A:
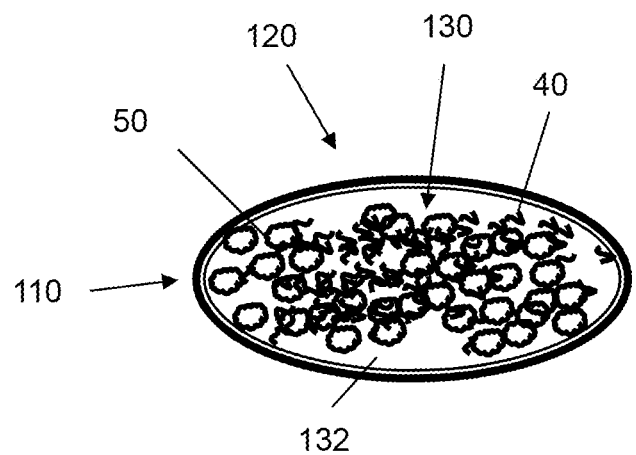
FIG. 3A depicts an exemplary delivery device, according to various embodiments of the present disclosure.

In some embodiments, barrier wall 36 may be optional. For example, an alternative device 110 is depicted in FIG. 3A as having an exterior layer 120 similar to exterior layer 20 of device 10, and an interior core 130 including a single compartment 132. Enzyme 40 and fat 50 may be stored within compartment 132 so that even though they are contained within the same compartment, they are not capable of reacting with one another. For example, enzyme 40 and fat 50 may be mixed in compartment 132 with only minimal amounts of a reactant that is necessary for the enzyme and the fat to react. For example, enzyme 40 and fat 50 may be contained in compartment 132 with little water, or with no water at all. Accordingly, compartment 132 may not contain enough of a reactant, e.g., water, to allow enzyme 40 to hydrolyze fat 50. Only a smaller, background amount of hydrolysis may occur within interior core 130 prior to dissolution of exterior layer 120, or no hydrolysis may occur at all. Upon dissolution of exterior layer 120 (which may be made up of a single layer or multiple layers), however, a larger effective amount of hydrolysis may occur within or outside of core 130 when portions of layer 120 or all of layer 120 dissolve.

Figure 3B:
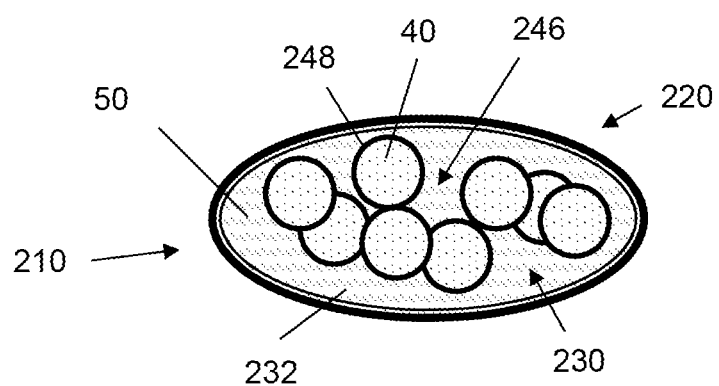
FIG. 3B depicts another exemplary delivery device, according to various embodiments of the present disclosure.

In some embodiments, enzyme 40 and/or fat 50 may be in a form that inhibits physical interaction until exposure to a trigger (e.g., a neutral to alkaline environment). In some embodiments, the form of either or both of enzyme 40 and fat 50 may prevent them from interacting with each other. For example, one or both may be stored in a solid phase or a gel phase that inhibits and/or slows interaction between the two until device 10 breaks down. In the embodiment of FIG. 3B, device 210 is depicted as having an exterior layer 220 similar to exterior layer 20 of device 10, and an interior core 230 including a single compartment 232. As shown in FIG. 3B, fat 50 may be contained in single compartment 232, and enzyme 40 may be contained within a plurality of interior capsules 246 suspended in fat 50 (or vice versa). Fat 50 may be stored in liquid form, and each interior capsule 246 may have an exterior layer 248 that is insoluble in the liquid fat 50, yet is soluble within the trigger environment, preventing hydrolysis until interior capsules 246 have been exposed to the trigger.

Although FIG. 3B depicts a plurality of interior capsules 246, it is contemplated that compartment 232 may contain one interior capsule 246, such that device 210 is essentially formed of a pill within a pill (compartment 232 forming the first, outer pill, and interior capsule 246 forming the second, interior pill). One or more interior capsules 246 may have any suitable shape or size (so long as they fit within compartment 232), and, if multiple interior capsules 246 are included, may have different shapes or sizes or the same shapes or sizes. For example, a device may include an outer compartment 232, which may contain a fat 50, which may be fish oil. Outer compartment 232 may also contain an interior capsule 246 within it. Interior capsule 246 may contain enzyme 40, which may be lipase. Outer compartment 232 may be formed of the same material as interior capsule 246 or may be formed of a different material. Additionally, outer compartment 232 may be configured to dissolve prior to interior capsule 246, after interior capsule 246, or concurrently with interior capsule 246.

Aspects of enzyme 40 and fat 50 may be modified for multiphasic delivery. For example, enzyme 40 and/or fat 50 may be multi-phased materials configured to dissolve and mix together in a time-release manner. Exemplary multiphasic materials may include one or more of: solids, powders, granules, crystals, hot melts, pastes, gels, liquids, coated materials, lipids, enrobed materials, softgels, nanomolecules, beadlets, microencapsulations, enchochleates, suspensions, emulsions, and/or gases. Enzyme 40 and fat 50 may include the same or different multiphasic materials.

Aspects of delivery device 10 also may be modified to promote delivery of its contents. As shown in FIG. 1, for example, exterior coating 26 may optionally include one or more dissolvable plugs 38 (depicted optionally with dotted lines). Each dissolvable plug 38 may extend through exterior coating 26 and, like the remainder of exterior coating 26, may be insoluble in a non-trigger environment and soluble in a trigger environment (e.g., insoluble in an acidic environment and soluble in a neutral to alkaline environment). Each plug 38, however, may have a dissolution rate that is faster than the dissolution rate of the remainder of exterior coating 26. The differences in dissolution rates between each plug 38 and the rest of exterior coating 26 may create openings in one or both of first and second compartments 32A and 32B. One dissolvable plug 38 may, as in FIG. 1, be located adjacent barrier wall 36 so that the resulting opening extends through capsule shell 22 and barrier wall 36, allowing enzyme 40 and fat 50 to mix inside of interior core 30 and/or to flow out of interior core 30. Additionally or alternatively, at least one dissolvable plug 38 may be located on each side of barrier wall 36, creating separate openings for first and second compartments 32A and 32B, allowing enzyme 40 and fat 50 to flow out separately and to mix inside of and/or outside of interior core 30.

As also shown in FIG. 1, at least first compartment 32A may optionally include one or more additional barrier walls 37 (depicted optionally with dotted lines), allowing a first portion of enzyme 40 to be released when barrier wall 36 is dissolved, and then allowing additional portions of enzyme 40 to be released as each additional boundary wall 37 is dissolved. For example, fat 50 of FIG. 1 may be a concentrated fat (e.g., powder, liquid, solution, etc.) and may have a slow dissolution rate. Dissolvable plug 38 may be used to mix a first amount of enzyme 40 with a first portion of the concentrated fat, and barrier wall 37 may be used to mix a second amount of enzyme 40 with a second portion of the concentrated fat, providing a more consistent flow of hydrolyzed fats to the body over longer periods of time and/or providing more complete and/or controlled mixing. Any number of additional boundary walls 37 may be provided, and additional boundary walls 37 may be located in one or both of first and second compartments 32A and/or 32B, to sequentially release amounts of enzyme 40 and/or fat 50.

Aspects of device 210 also may be modified to promote multiphasic delivery. For example, interior core 230 may include one or more barrier walls that package portions of the plurality of inner capsules 246 together with amounts of fat 50, creating multiple doses or a single slow-release dose in a single device 210. As a further example, the exterior layers 248 of some capsules 246 may have dissolution rates that are different (e.g., slower) than the exterior layers 248 of other capsules 246 to stagger the release of enzyme 40 (or vice versa if enzyme 40 is stored within interior core 230 and fat 50 is stored within capsules 246).

Figure 4:
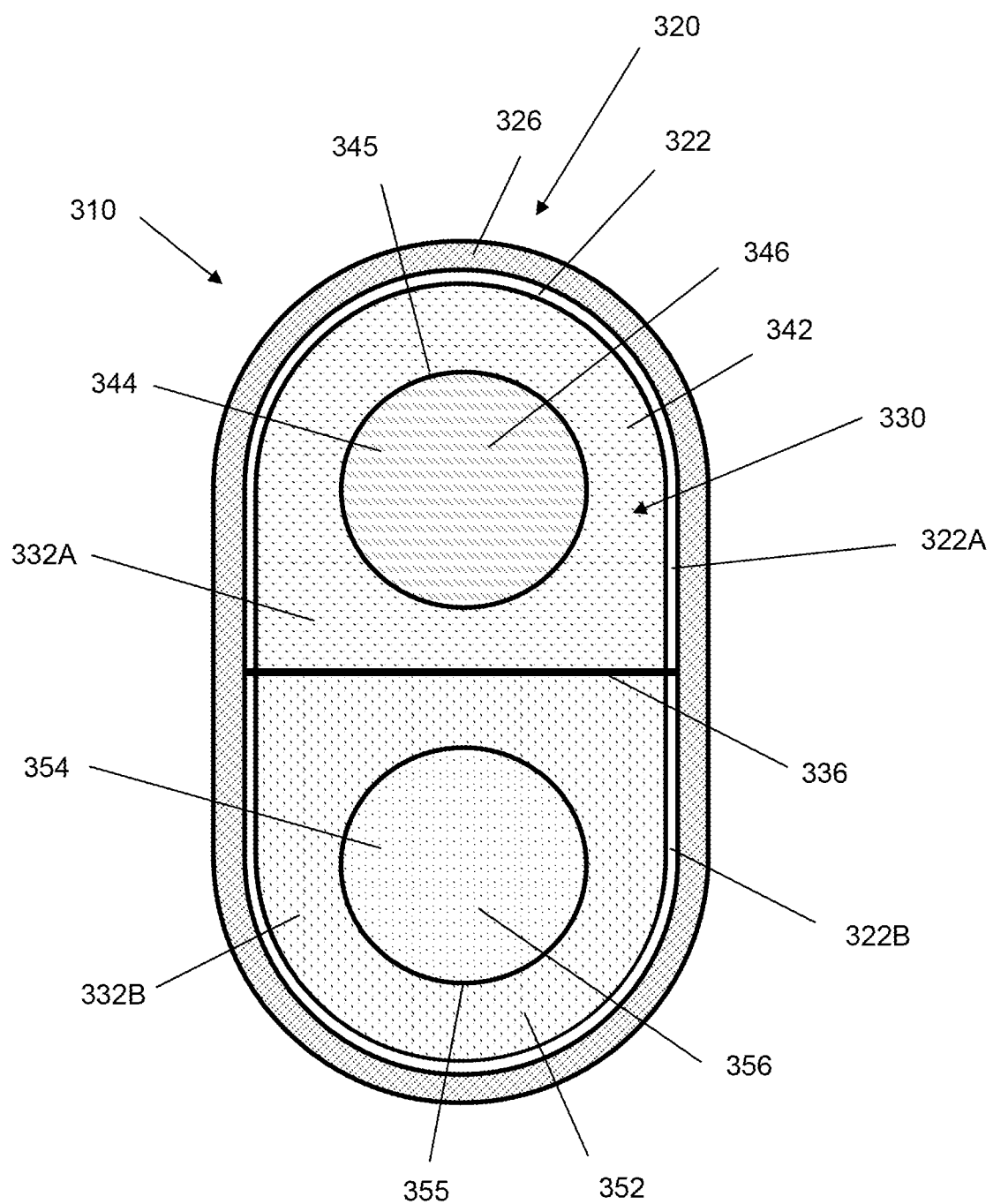
FIG. 4 depicts another exemplary delivery device, according to various embodiments of the present disclosure.

Aspects of device 10 (or any of the exemplary devices described herein) also may be modified to deliver enzymes and fats together with other supplements. One exemplary device 310 is depicted in FIG. 4. Device 310 comprises an exterior layer 320 surrounding an interior core 330. Exterior layer 320 may include a capsule shell 322 formed by joining two portions 322A and 322B using an exterior coating 326, or other suitable mechanisms, as described above in reference to device 10. As before, exterior layer 320 may be insoluble within a non-target environment (e.g., an acidic environment like the stomach), and soluble in a target environment (e.g., a neutral to alkaline environment). Interior core 330, similar to interior core 30, may include a first compartment 332A defined by interior surfaces of first portion 322A of exterior layer 320, a second compartment 332B defined by interior surfaces of second portion 322B of exterior layer 320, and a barrier wall 336 extending therebetween. Also as before, at least portions of interior core 330, such as barrier wall 336, may be soluble in the target environment.

As shown in FIG. 4, first compartment 332A may comprise a first supplement 342, at least one first interior capsule 344, and a first enzyme 346 contained within first interior capsule(s) 344. Each first interior capsule 344 may include an outer layer 345 that is insoluble in first supplement 342, but that is soluble within the target environment. Second compartment 332B may comprise a second supplement 352, at least one second interior capsule 354, and a second enzyme 356 contained within second interior capsule(s) 354. Each second interior capsule 354 may likewise include an outer layer 355 that is insoluble in second supplement 352, but that is soluble within the target environment. Any number of capsules 344, 354 may be included within first and/or second compartments 332A and 332B. For example, a plurality of capsules 344 and 354 may included in each compartment 332A and 332B. If multiple capsules 344, 354 are included, the capsules may contain the same or different enzymes and/or other contents.

According to one aspect, first supplement 342 may include a fat, exterior layer 345 of first interior capsule 344 may include an enteric material, and first enzyme 346 may include a lipase enzyme. First enzyme 346 may remain separated from first supplement 342 until first compartment 332A and exterior layer 345 have been opened, for example, by exposure to the trigger environment. Once released, first enzyme 346 may mix with first supplement 342, causing hydrolysis of first supplement 342.

Second supplement 352 may include a protein, exterior layer 355 of second interior capsule 354 may include an enteric material, and second enzyme 356 may include a protease enzyme. Second enzyme 356 may remain separated from second supplement 352 until second compartment 332B and exterior layer 355 have been opened by exposure to the trigger environment. Once released, second enzyme 356 may mix with second supplement 352, causing hydrolysis of second supplement 352. Any combination of enzymes and supplements may be used. For example, in another embodiment, second capsule 354 may include an amylase enzyme, and second compartment 332B may include a carbohydrate.

In some embodiments, it is understood that the trigger for first compartment 332A and exterior layer 345 may be different than the trigger for second compartment 332B and exterior layer 355, and/or first compartment 332A and exterior layer 345 may have different dissolution rates than second compartment 332B and exterior layer 355. Accordingly, in some embodiments, the reactions between first supplement 342 and first enzyme 346 may occur at a different time and/or different location in the body than second supplement 352 and second enzyme 356. In some embodiments, first supplement 342 and second supplement 352 and/or first enzyme 346 and/or second enzyme 356 may be the same supplement and/or the same enzyme. Additionally, as described previously, any number of compartments and/or or capsules may be included in devices of the present disclosure.

Without deviating from this disclosure, aspects of devices 10, 110, 210, and/or 310 may be further modified to promote hydrolysis. For example, either or both of enzyme 40 and/or fat 50 may include a hydrolyzing catalyst, such as water. In some embodiments, water may be stored in a separate compartment and/or in a compartment with another material (e.g., a fat). Any of barrier walls 36 and/or 37 of device 10 may have one or more interior portions including a catalyst, and the interior portions may be opened with each wall 36 or 37 to release the catalyst. For device 210, one or more of the plurality of interior capsules 246 may include a catalyst. And for device 310, one or both of first supplement 342 or second supplement 352 of device 310 may include a catalyst.

Numerous different aspects of devices 10, 110, 210, and 310 have been described. Each of these aspects are interchangeable, such that aspects described with reference to device 10 may be incorporated into any of devices 110, 210, or 310, and vice versa, each potential iteration being part of this disclosure. However configured, the described aspects provide various mechanisms for mixing various enzymes, fats, and/or other supplements once the delivery devices have been ingested by the body. In some embodiments, the delivery devices may mix the various contents within specific regions within the body. Additionally, single phasic and multiphasic aspects are described. Such embodiments may allow the mixing and/or the releasing to occur at once or over a period time. Particular aspects include a lipase enzyme configured to hydrolyze fats to promote the delivery of hydrolyzed fats (e.g., free fatty acid, monoglyceride) to, for example, the intestine (e.g., the small intestine) to promote the absorption of hydrolyzed fats by the body.

As discussed above, devices disclosed herein may, in some aspects, allow hydrolyzed fatty acids (monoglycerides and free fatty acids) to be delivered to and absorbed by the body without the consumption of food. The absorption of some fatty acids, e.g., EPA, DHA, and omega-3-acid ethyl esters (EEs) may be influenced by the presence of food. Several studies have shown that the bioavailability of prescription omega-3 acid EE formulations is highly impacted by concomitant food intake, particularly the fat content of the food. Whereas free fatty acid forms of EPA and DHA do not require pancreatic enzyme activity for digestion, EPA and DHA EEs may require additional digestion with carboxyl ester lipase (also known as bile salt-dependent lipase), the release into the intestine of which is highly dependent on the presence of fat in the diet. Accordingly, if taken alone, fish oils and other fats may need to be consumed with food in order for the body to effectively break down and absorb them. As a result, there has been a need for a formulation of fatty acids that is less impacted by the food effect. Because the devices described herein provide fats in addition to lipase, the provided lipase may hydrolyze the fats into a form that is readily absorbed by the body, even without the presence of food. Accordingly, the devices described herein may be able to be consumed without food while still allowing the body of the consumer to uptake the provided fats. Devices described herein may therefore fulfill the need for a formulation that optimizes the bioavailability of free fatty acids within the body even without the presence of food in the body.

The ability to consume, e.g., devices 10, 110, 210, and 310 without food may be beneficial to a number of different patient populations, including, but not limited to, those suffering from traumatic brain injury (TBI). TBI, such as, but not limited to, concussion, is characterized by neuroinflammation. Currently, the standard of care in the treatment for concussions is typically cognitive and physical rest until symptoms resolve, with a graduated return to activity. However, high dose omega-3 fatty acids have shown to have anti-inflammatory, anti-oxidant, and membrane-stabilizing properties. For example, long-chain omega-3 fatty acids, such as EPA and DHA, have anti-inflammatory properties. Since they can pass through the blood-brain barrier, EPA and DHA have the potential to reduce the neuro-inflammation that accompanies TBI. Accordingly, without being bound to the theory, nutrition interventions may present a safe and low-risk option for protection against and/or reduction in sub-concussive impacts. DHA is the principal omega-3 polyunsaturated fatty acid in the brain, and plays a role in the brain's development and structural integrity.

Primary brain injury, the initial physical injury to brain tissue post-trauma, is believed to respond only to measures that prevent TBI from occurring in the first place. However, secondary brain injury, which is, generally speaking, a cascade of events causing additional brain injury following primary brain injury, may be more amenable to pharmacologic treatment. Neuroinflammation is one of the recognized mechanisms of secondary brain injury. In response to primary brain injury, activated microglia and injured neurons both release signaling proteins, including cytokines and chemokines. Omega-3 and omega-6 fatty acids are major components of immune cells and neuronal cell membranes. They are also precursors to neuromodulatory lipids, such as eicodanoids, endovanilloids, and endocannabinoids that have antinociceptive and anxiolytic properties. DHA is one of the most abundant fatty acid components of brain cell membrane phospholipids.

Rodent studies have indicated that dietary supplementation with omega-3 fatty acids (EPA and DHA) may decrease secondary axonal injury, attenuated endoplasmic reticulum stress response, and neuroinflammation post-TBI, and may improve short- and long-term neurologic outcomes. Additionally, DHA supplementation post-TBI may enhance neurogenesis by counteracting reductions in neuroplasticity biomarkers, such as brain-derived neurotrophic factor. Furthermore, studies have indicated that DHA-deficient rodents are more likely to have a greater amount of axonal injury and slower recovery neurologic recovery post-TBI. Additionally, a prior study was conducted on collegiate football players who were randomized to 2, 4, or 6 g/day of DHA or placebo for a total of 189 days (including 80 pre-season days). Irrespective of the dose of DHA supplementation, those receiving DHA had lower values of serum neurofilament light chain, a biomarker of axonal injury, than those receiving placebo.

In exemplary embodiments of the disclosure, a device (e.g., device 10, 110, 210, 310) containing a lipid (e.g., omega-3 fatty acids) in one compartment and lipase in another compartment may be used to promote hydrolysis and absorption of the lipid (e.g., omega-3 fish oil) in the higher-absorption regions in the small intestine. This may be done without requiring food to promote absorption of the hydrolyzed lipid by the body. As discussed above, omega-3 fatty acids may have anti-inflammatory properties, but current preparations of omega-3 fish oil capsules have limited bioavailability if taken without food, e.g., on an empty stomach. By way of example, a patient who is seen in an emergency room or urgent care center, suspected of having sustained a concussion, may not have recently eaten food. For example, a sports player is likely to be in a fasting state if playing in a game. A person with TBI may be too disoriented to eat, or it may not be desirable for the person to eat in case the severity of the head injury or other injuries requires further medical treatment (e.g., surgery). Yet, without feeding a person, upon treatment with fatty acids like omega-3 oil, the person would not be in the proper fed state to fully absorb the omega-3 oil at the time of treatment and thus may not receive the benefits of the treatment.

The devices disclosed herein, however, may address this issue, and others, by delivering both fats, e.g., omega-3 fish oil, along with a lipase to promote hydrolysis and absorption of the omega-3 fish concurrently in the higher-absorption regions in the intestine (e.g., the small intestine). Because the fat is delivered with lipase, the fat may be broken down into a bioavailable form (monoglycerides and free fatty acids) even without the presence of food, allowing the disclosed devices to be administered without food and/or on an empty stomach. Further, as discussed previously, by separating lipase and fat within the device, the device may overcome issues pertaining to oxidation of the fats (e.g., triglyceride fish oil).

In an exemplary method of treatment using the devices described herein, a person suspected of TBI may be administered an oral bolus dose of lipase and fats using one of the disclosed devices upon suspected concussion, followed by twice-a-day dosing of, e.g., 4 grams of omega-3 fish oil. Therapy may be continued for 90 days or until symptoms resolve. In at least some instances, the person would be in the fasted state during consumption of the disclosed devices to ensure optimal absorption of the omega-3 fatty acid and/or other anti-inflammatory ingredients, unobstructed by previously consumed food, which may inhibit optimal absorption. Because devices of the present disclosure may be administered on an empty stomach and/or without food, the hydrolyzed fatty acids delivered to the body may not be in competition with other food products to be taken up by the body. This may also increase absorption of hydrolyzed fats, like omega-3 fatty acids, providing another benefit currently unobtainable with known devices because of the need for concurrent food consumption.

In some aspects, devices described herein may be administered to a person with suspected TBI immediately after the injury, for example, on the sidelines at a sporting event or on the battlefield. Devices of the present disclosure may be kept in a first-aid kit and may be given prior to sending the person to the emergency room or being seen by a doctor, since fats and lipase are safe to administer even if the person is not ultimately diagnosed with TBI. For example, devices of the present disclosure may be administered within minutes (e.g., within 1, 2, 5, 10, 15, or 20 minutes) of the suspected injury, or within hours (e.g., within 1, 2, 3, 4, or 5 hours) of the suspected injury. Further, in some aspects, disclosed devices may be administered before injury to provide a protective effect on brain cells. For example, ingestible delivery devices according to the present disclosure may be ingested daily, multiple times a day, before an activity (e.g., a physical activity, like a sports game or practice, or before a dangerous activity, like conducting military operations or a rescue mission), or otherwise on a regular basis.

Medical personnel, a parent, a coach, or the person with suspected injury (or even before injury), e.g., may administer an ingestible delivery device according to the disclosed embodiments, which may include, e.g., 2 grams of a omega-3, 500 mg resveratrol, and/or 200 mgs co-enzyme Q10. In some embodiments, an ingestible delivery device may include one or more of the following ingredients, in combination with lipase and/or fat (e.g., an omega-3 fatty acid): resveratrol, magnesium, co-enzyme Q-10, curcumin, turmeric, creatine, melatonin, vitamin B2 (riboflavin), *S. baicalensis*, n-acetyl cysteine (NAC), and/or any supplement with potential anti-inflammatory properties. The additional ingredients may be separated from each other and/or the lipase and fat, and/or may be combined in at least one chamber. Additional examples of combinations of ingredients are set forth below:

- a combination of resveratrol and omega-3 in one chamber, lipase in a separate chamber
- a combination of resveratrol, curcumin, and omega-3 in one chamber, lipase in a separate chamber
- a combination of resveratrol, curcumin, magnesium, and omega-3 in one chamber, lipase in a separate chamber
- a combination of resveratrol, curcumin, magnesium, co-enzyme Q-10, and omega-3 in one chamber, lipase in a separate chamber
- a combination of resveratrol, curcumin, magnesium, co-enzyme Q-10, turmeric, and omega-3 in one chamber, lipase in a separate chamber
- a combination of resveratrol, curcumin, magnesium, co-enzyme Q-10, turmeric, creatine, and omega-3 in one chamber, lipase in a separate chamber
- a combination of resveratrol, curcumin, magnesium, co-enzyme Q-10, turmeric, creatine, melatonin, and omega-3 in one chamber, lipase in a separate chamber
- a combination of resveratrol, curcumin, magnesium, co-enzyme Q-10, turmeric, creatine, melatonin, vitamin B2, and omega-3 in one chamber, lipase in a separate chamber
- a combination of resveratrol, curcumin, magnesium, co-enzyme Q-10, turmeric, creatine, melatonin, vitamin B2, *S. baicalensis*, and omega-3 in one chamber, lipase in a separate chamber
- a combination of resveratrol, curcumin, magnesium, co-enzyme Q-10, turmeric, creatine, melatonin, vitamin B2, *S. baicalensis, n*-acetyl cysteine (NAC), and omega-3 in one chamber, lipase in a separate chamber The above listing of ingredients is by no means limiting, and more or fewer ingredients may be contained within devices of the present disclosure. Additionally, ingredients may be separated, and/or combined between any suitable number of compartments.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents that all fall in the scope of the aspects described herein. Accordingly, the present disclosure is not to be considered as limited by the foregoing description.

What is claimed is:

1. An ingestible delivery device comprising:
a first compartment;
a second compartment;
a lipase contained within the first compartment; and
a fat contained within the second compartment;
wherein the first compartment is sealed from the second compartment by a barrier wall prior to exposure to a trigger, the barrier wall preventing the lipase and the fat from contacting each other, and wherein at least a portion of the barrier wall at least partially ruptures upon exposure to the trigger, allowing the lipase and the fat to contact each other,
wherein the barrier wall partitions the ingestible delivery device into the first compartment and the second compartment, and wherein the trigger is at least one of a neutral pH or an alkaline pH.

2. The device of claim 1, further comprising an exterior layer surrounding the first compartment and the second compartment.

3. The device of claim 1, further comprising a third compartment and at least one of a protein, a protease, a carbohydrate, or an amylase contained within the third compartment.

4. The device of claim 3, further comprising a fourth compartment and at least one of a protein, a protease, a carbohydrate, or an amylase contained within the fourth compartment.

5. The device of claim 1, wherein the first compartment is contained within the second compartment.

6. The device of claim 1, wherein the fat includes at least one of a structured lipid, a short-chain fatty acid, a medium-chain fatty acid, or a long-chain fatty acid.

7. The device of claim 1, wherein the fat is an omega-3 fatty acid, and wherein the device further comprises at least one of resveratrol, curcumin, magnesium, co-enzyme Q10, turmeric, or creatine.

8. An ingestible delivery device comprising:
a plurality of compartments;
a lipase contained within a first compartment of the plurality of compartments;
a fat contained within a second compartment of the plurality of compartments; and
a barrier wall extending between and separating the first compartment from the second compartment, wherein the barrier wall separates the lipase and the fat when the barrier wall is in a first state, and wherein the barrier wall at least partially degrades in response to a trigger to expose the lipase to the fat when the barrier wall is in a second state;
wherein the trigger is at least one of a neutral pH or an alkaline pH.

9. The device of claim 8, wherein the fat includes at least one of a structured lipid, a short-chain fatty acid, a medium-chain fatty acid, or a long-chain fatty acid.

10. The device of claim 8, further comprising a third compartment of the plurality of compartments, wherein the third compartment contains at least one of a protease or an amylase.

11. The device of claim 10, further comprising a fourth compartment, wherein the fourth compartment contains at least one of a protein or a carbohydrate.

12. The device of claim 8, wherein the fat is an omega-3 fatty acid, and wherein the device further comprises at least one of resveratrol, curcumin, magnesium, co-enzyme Q10, turmeric, or creatine.

13. The device of claim 1, further comprising a third compartment containing a protein and a fourth compartment containing a protease.

14. The device of claim 13, wherein the fourth compartment is contained in the third compartment.

15. The device of claim 11, wherein the third compartment contains the protease and the fourth compartment contains the protein.

16. The device of claim 15, wherein the third compartment is contained in the fourth compartment.

17. The device of claim 16, wherein a second barrier wall separates the third compartment and the fourth compartment.

18. An ingestible delivery device comprising:
a first compartment containing a lipase;
a second compartment containing a fat;
a third compartment containing a protein; and
a fourth compartment containing a protease;
wherein an interior region of each of the first compartment, the second compartment, the third compartment, and the fourth compartment is isolated so that the lipase, the fat, the protein, and the protease are isolated from each other in a first state, and wherein at least one of the lipase, the fat, the protein, or the protease is exposed to at least one other of the lipase, the fat, the protein, or the protease in a second state;

wherein the ingestible delivery device transitions from the first state to the second state in response to at least one of a neutral pH or an alkaline pH.

19. The device of claim 18, further comprising an exterior layer surrounding the plurality of compartments.

20. The device of claim 18, wherein a capsule shell surrounds the first compartment, the second compartment, the third compartment, and the fourth compartment.

* * * * *